US010653429B2

(12) United States Patent
Baril et al.

(10) Patent No.: US 10,653,429 B2
(45) Date of Patent: May 19, 2020

(54) ENDOSCOPIC SURGICAL CLIP APPLIER

(71) Applicant: Covidien LP, Mansfield, MA (US)

(72) Inventors: Jacob C. Baril, Norwalk, CT (US);
Brian J. Creston, West Haven, CT (US); Roman Czernik, Trumbull, CT (US); Thomas A. Zammataro, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 170 days.

(21) Appl. No.: 16/042,227

(22) Filed: Jul. 23, 2018

(65) Prior Publication Data
US 2019/0076149 A1 Mar. 14, 2019

Related U.S. Application Data

(60) Provisional application No. 62/557,908, filed on Sep. 13, 2017.

(51) Int. Cl.
A61B 17/128 (2006.01)
A61B 17/00 (2006.01)

(52) U.S. Cl.
CPC .. *A61B 17/1285* (2013.01); *A61B 2017/0046* (2013.01)

(58) Field of Classification Search
CPC ........ A61B 17/1285; A61B 2017/0046; A61B 17/128; A61B 17/10; A61B 34/70; A61B 2017/0488
See application file for complete search history.

(56) References Cited

U.S. PATENT DOCUMENTS

| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |

(Continued)

FOREIGN PATENT DOCUMENTS

| AU | 2013254887 A1 | 11/2013 |
| CA | 1163889 A | 3/1984 |

(Continued)

OTHER PUBLICATIONS

The extended European Search Report corresponding to European Application No. EP 07 25 3905.9, completed Jan. 29, 2008; dated Feb. 7, 2008; (7 Pages).

(Continued)

*Primary Examiner* — Tan-Uyen T Ho
*Assistant Examiner* — Lee O Chedister
(74) *Attorney, Agent, or Firm* — Carter, DeLuca & Farrell LLP

(57) ABSTRACT

A shaft assembly of an apparatus for applying surgical clips to body tissue includes a pair of jaws movable between a spaced-apart position and an approximated position, an elongated spindle, a shaft, a slidable member, and a pusher bar fixed to the slidable member. The slidable member is movable through longitudinally-extending channels of the spindle and the shaft. The pusher bar is configured to load a distal-most surgical clip into the pair of jaws during distal movement of the slidable member, via distal movement of the spindle, and remain in a distally advanced position during approximation of the pair of jaws.

20 Claims, 10 Drawing Sheets

(56) References Cited

U.S. PATENT DOCUMENTS

| | | |
|---|---|---|
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |

(56) References Cited

U.S. PATENT DOCUMENTS

| | | |
|---|---|---|
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sheds et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |

(56) References Cited

U.S. PATENT DOCUMENTS

| | | |
|---|---|---|
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |

(56) References Cited

U.S. PATENT DOCUMENTS

| | | |
|---|---|---|
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |

(56) References Cited

U.S. PATENT DOCUMENTS

| | | |
|---|---|---|
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0014060 A1* | 1/2003 | Wilson, Jr. ......... A61B 17/1285 606/142 |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0093856 A1* | 4/2007 | Whitfield ......... A61B 17/1285 606/142 |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |

(56) References Cited

U.S. PATENT DOCUMENTS

| | | |
|---|---|---|
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1* | 5/2017 | Holsten ............ A61B 17/105 |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0076149 A1* | 3/2019 | Baril ............... A61B 17/1285 |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 2609877 A1 | 7/2013 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| WO | 0042922 A1 | 7/2000 |
| WO | 0166001 A2 | 9/2001 |
| WO | 0167965 A1 | 9/2001 |
| WO | 2015069719 A1 | 5/2015 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

International Search Report corresponding to International Application No. PCT-US08-58185, completed Sep. 4, 2008; dated Sep. 9, 2008; (2 Pages).

The International Search Report corresponding to International Application No. PCT-US08-59859, completed Sep. 14, 2008; dated Sep. 18, 2008; (2 Pages).

The extended European Search Report corresponding to European Application No. EP 07 25 3807.7, completed Nov. 7, 2008; dated Nov. 26, 2008; (11 Pages).

The extended European Search Report corresponding to European Application No. EP 09 25 2049.3, completed Dec. 11, 2009; dated Jan. 12, 2010; (3 Pages).

The extended European Search Report corresponding to European Application No. EP 09 25 2050.1, completed Dec. 23, 2009; dated Jan. 21, 2010; (3 Pages).

The extended European Search Report corresponding to European Application No. EP 09 25 2051.9, completed Dec. 21, 2009; dated Jan. 28, 2010; (3 Pages).

The extended European Search Report corresponding to European Application No. EP 09 25 2052.7, completed Nov. 16, 2009; dated Nov. 24, 2009; (3 Pages).

The extended European Search Report corresponding to European Application No. EP 09 25 2053.5, completed Nov. 24, 2009; dated Dec. 1, 2009; (3 Pages).

The extended European Search Report corresponding to European Application No. EP 09 25 2054.3, completed Jan. 7, 2010; dated Jan. 22, 2010; (3 Pages).

(56) References Cited

OTHER PUBLICATIONS

The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
International Search Report and Written Opinion issued by the Korean Intellectual Property Office, acting as the International Searching Authority, dated Jan. 21, 2019 in corresponding International Application No. PCT/US2018/050349.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.

(56) References Cited

OTHER PUBLICATIONS

Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

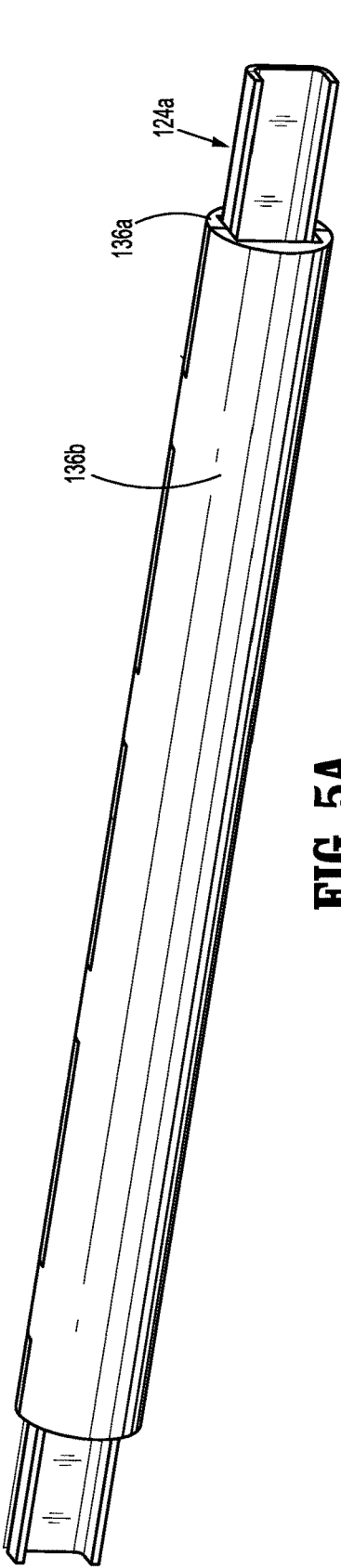
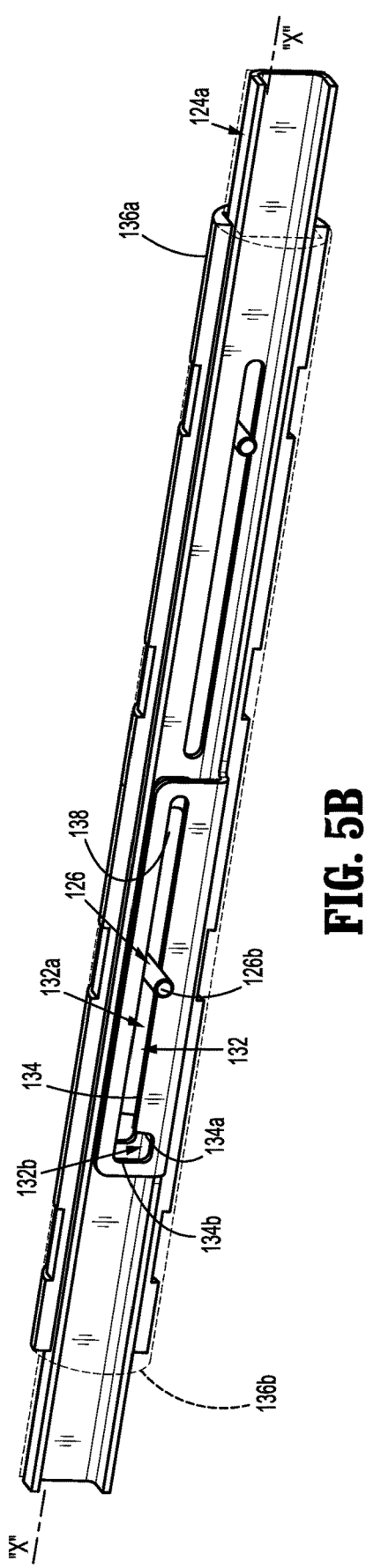
FIG. 5A
FIG. 5B

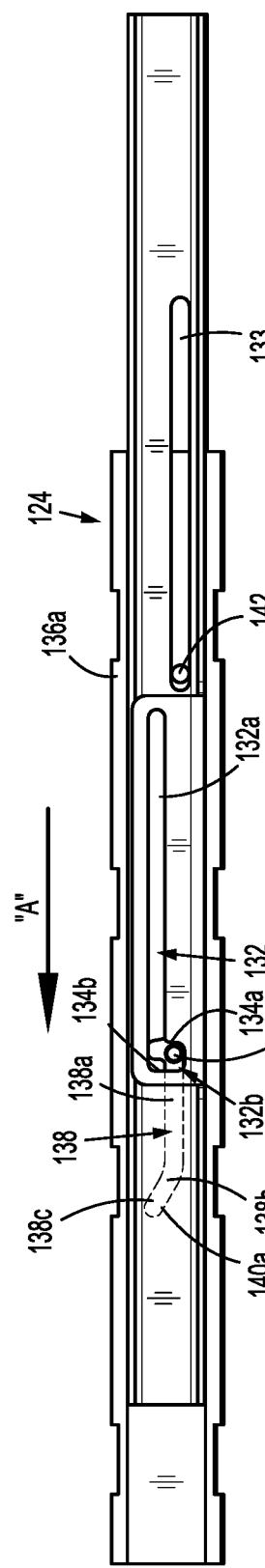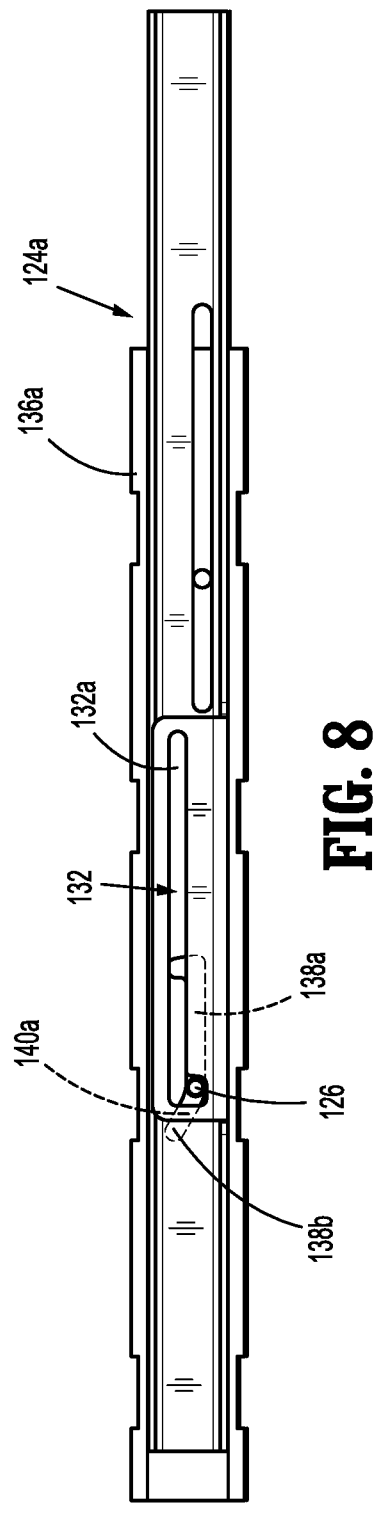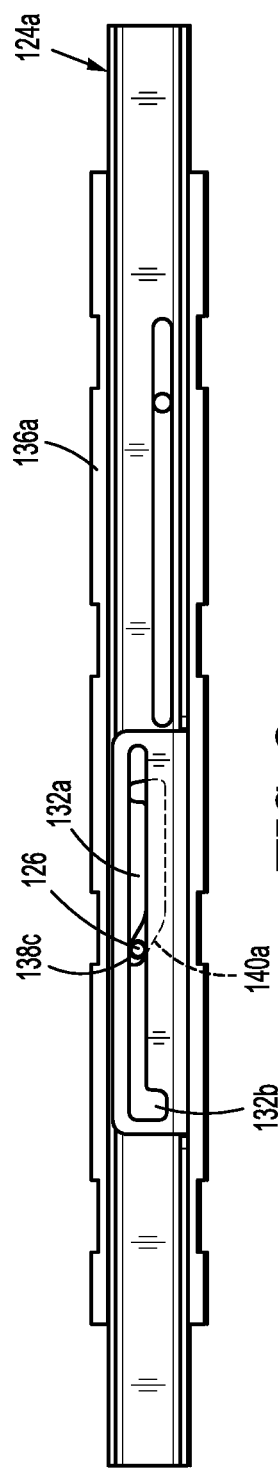

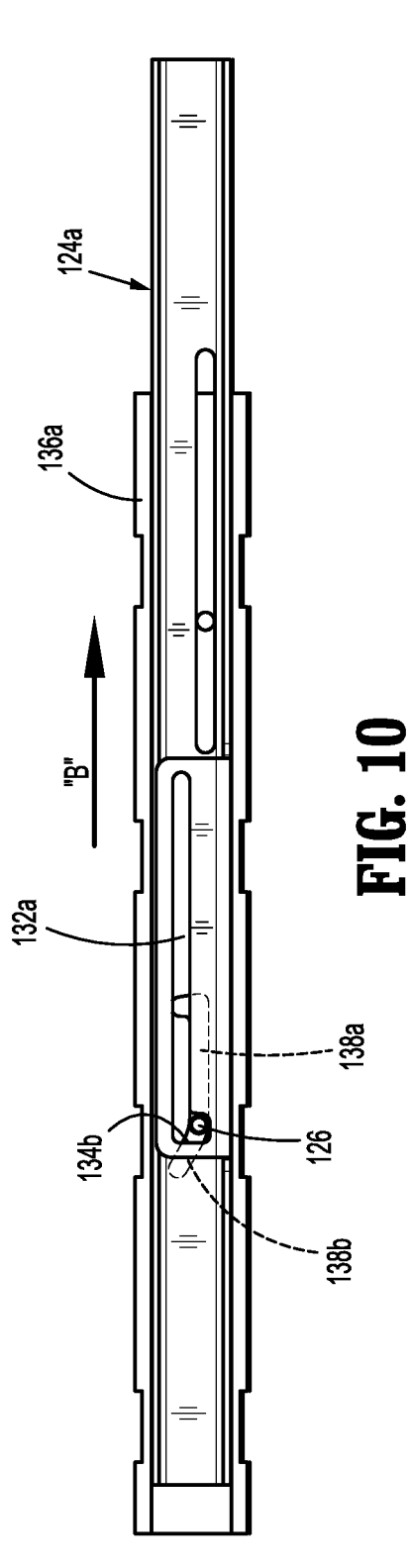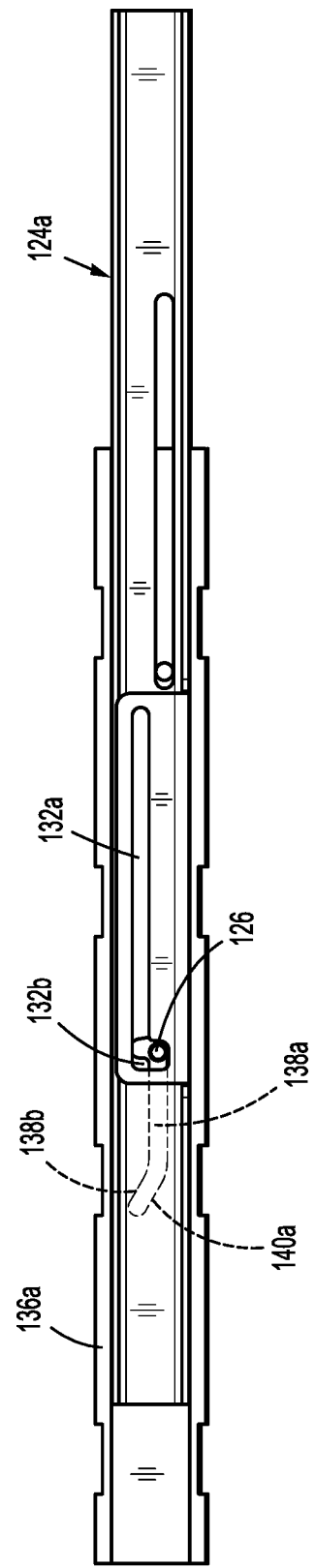

ENDOSCOPIC SURGICAL CLIP APPLIER

CROSS-REFERENCE TO RELATED APPLICATIONS

This application claims the benefit of and priority to U.S. Provisional Patent Application No. 62/557,908 filed Sep. 12, 2017, the entire disclosure of which is incorporated by reference herein.

BACKGROUND

Technical Field

The present application relates generally to surgical clip appliers. More particularly, the present disclosure relates to endoscopic surgical clip appliers having a clip pusher bar that maintains a surgical clip between jaws of the surgical clip applier during clip formation.

Description of Related Art

Endoscopic surgical staplers and surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often use a particular endoscopic surgical clip applier to apply a surgical clip to a blood vessel or another duct to prevent the flow of body fluids therethrough during the procedure.

Endoscopic surgical clip appliers having various sizes (e.g., diameters) that are configured to apply a variety of diverse surgical clips are known in the art, and which are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

Endoscopic surgical clip appliers that are able to apply multiple clips in endoscopic or laparoscopic procedures during a single entry into the body cavity are described in commonly-assigned U.S. Pat. Nos. 5,084,057 and 5,100,420, which are both incorporated by reference herein in their entirety. Another multiple endoscopic surgical clip applier is disclosed in commonly-assigned U.S. Pat. No. 5,607,436, the contents of which are also hereby incorporated by reference herein in its entirety. These devices are typically, though not necessarily, used during a single surgical procedure. U.S. Pat. No. 5,695,502, the disclosure of which is hereby incorporated by reference herein, discloses a resterilizable endoscopic surgical clip applier. The endoscopic surgical clip applier advances and forms multiple clips during a single insertion into the body cavity. This resterilizable endoscopic surgical clip applier is configured to receive and cooperate with an interchangeable clip magazine so as to advance and form multiple clips during a single entry into a body cavity.

Sometimes prior to or during formation of the clip, the clip may be prematurely dislocated from between the jaws of the clip applier by, for example, the vessel being closed. Accordingly, a need exists for a clip applier having an improved mechanism that prevents clip dislocation during use.

SUMMARY

Accordingly, the present application provides an apparatus for application of surgical clips to body tissue. The apparatus includes a handle assembly and a shaft assembly selectively connectable to the handle assembly and actuatable upon actuation of the handle assembly. The shaft assembly includes a pair of jaws movable between a spaced-apart position and an approximated position, an elongated spindle, a first shaft disposed alongside the spindle, a slidable member, and a pusher bar having a proximal portion fixed to the slidable member. The spindle has a proximal portion configured to be coupled to an actuator of the handle assembly, and a distal portion operably coupled to the pair of jaws to selectively approximate the pair of jaws during distal movement of the spindle. The spindle defines a longitudinally-extending channel having a first portion, and a second portion extending at a non-zero angle relative to the first portion. The first shaft defines a longitudinally-extending channel having a first portion, and a second portion extending at a non-zero angle relative to the first portion of the channel of the first shaft. The slidable member extends through each of the channels, and a first distal movement of the spindle relative to the first shaft moves the slidable member with the spindle and through the first portion of the channel of the first shaft. A second distal movement of the spindle relative to the first shaft moves the slidable member with the spindle and into the second portion of the channel of the first shaft and the first portion of the channel of the spindle. A third distal movement of the spindle relative to the first shaft moves the spindle distally relative to the slidable member. The pusher bar has a distal portion configured to load a distal-most surgical clip into the pair of jaws during distal movement of the slidable member, via the first distal movement of the spindle, and remain in a distally advanced position during approximation of the pair of jaws.

In embodiments, the first portion of the channel of each of the spindle and the first shaft may have a linear configuration and extend parallel to a longitudinal axis defined by the spindle, and the second portion of the channel of each of the spindle and the first shaft may extend at a non-parallel angle relative to the longitudinal axis of the spindle.

It is contemplated that the shaft assembly may further include a second shaft disposed on an opposite side of the proximal portion of the spindle as the first shaft. The second shaft may be fixedly coupled to the first shaft and define a longitudinally-extending channel in mirrored relation with the channel of the first shaft. The slidable member may have a first end portion movably disposed within the channel of the first shaft, and a second end portion movably disposed within the channel of the second shaft.

It is envisioned that the first portion of the channel of the spindle may define a first plane, and the first portion of the channel of the first shaft may define a second plane offset from the first plane of the first portion of the channel of the spindle. A distal region of the second portion of the channel of the first shaft may be coplanar with the first plane of the first portion of the channel of the spindle.

In embodiments, the second portion of the channel of the spindle may have a proximal limit defined by a proximal wall. The proximal wall may be configured to contact the slidable member during the first distal movement of the spindle to distally move the slidable member relative to the first shaft.

It is contemplated that the second portion of the channel of the spindle may have a distal limit defined by a distal wall. The distal wall may be configured to contact the slidable member during proximal movement of the spindle relative to the first shaft.

It is envisioned that the first shaft may include a ramped inner surface that defines the second portion of the channel of the first shaft. The ramped inner surface may be configured to move the slidable member upwardly from the second portion of the channel of the spindle into the first portion of the channel of the spindle during the second distal movement of the spindle.

In embodiments, the slidable member may be axially restrained within the second portion of the channel of the first shaft during the third distal movement of the spindle, such that the pusher bar is axially fixed relative to the pair of jaws during the third distal movement of the spindle.

It is contemplated that the slidable member may ride within the first portion of the channel of the spindle during the third distal movement of the spindle.

In another aspect of the present disclosure, a shaft assembly of an apparatus for applying surgical clips to body tissue is provided. The shaft assembly includes a pair of jaws movable between a spaced-apart position and an approximated position, an elongated spindle, a first shaft disposed alongside the spindle, a slidable member, and a pusher bar having a proximal portion fixed to the slidable member. The spindle has a proximal portion configured to be coupled to an actuator, and a distal portion operably coupled to the pair of jaws to selectively approximate the pair of jaws during distal movement of the spindle. The spindle defines a longitudinally-extending channel having a first portion, and a second portion extending at a non-zero angle relative to the first portion. The first shaft defines a longitudinally-extending channel having a first portion, and a second portion extending at a non-zero angle relative to the first portion of the channel of the first shaft. The slidable member extends through each of the channels, and a first distal movement of the spindle relative to the first shaft moves the slidable member with the spindle and through the first portion of the channel of the first shaft. A second distal movement of the spindle relative to the first shaft moves the slidable member with the spindle and into the second portion of the channel of the first shaft and the first portion of the channel of the spindle. A third distal movement of the spindle relative to the first shaft moves the spindle distally relative to the slidable member. The pusher bar has a distal portion configured to load a distal-most surgical clip into the pair of jaws during distal movement of the slidable member, via the first distal movement of the spindle, and remain in a distally advanced position during approximation of the pair of jaws.

BRIEF DESCRIPTION OF THE DRAWINGS

A particular embodiment of a surgical clip applier is disclosed herein with reference to the drawings wherein:

FIG. 5A is a perspective view of a proximal portion of a spindle and left and right shafts of the shaft assembly of FIG. 3;

FIG. 5B is a perspective view, with a left shaft shown in phantom, of a proximal portion of the spindle and a slidable member of the shaft assembly of FIG. 3;

FIG. 7 is a side view of the proximal portion of the spindle and the slidable member of FIG. 5B, illustrating the spindle in a first, starting position;

FIG. 8 is a side view of the proximal portion of the spindle and the slidable member of FIG. 5B, illustrating the spindle in a second, staple loading position;

FIG. 9 is a side view of the proximal portion of the spindle and the slidable member of FIG. 5B, illustrating the spindle in a third, stapling forming position;

FIG. 10 is a side view of the proximal portion of the spindle and the slidable member of FIG. 5B, illustrating the spindle in a retracting position;

FIG. 11 is a side view of the proximal portion of the spindle and the slidable member of FIG. 5B, illustrating the spindle in a reset position;

DETAILED DESCRIPTION

Figure 1:
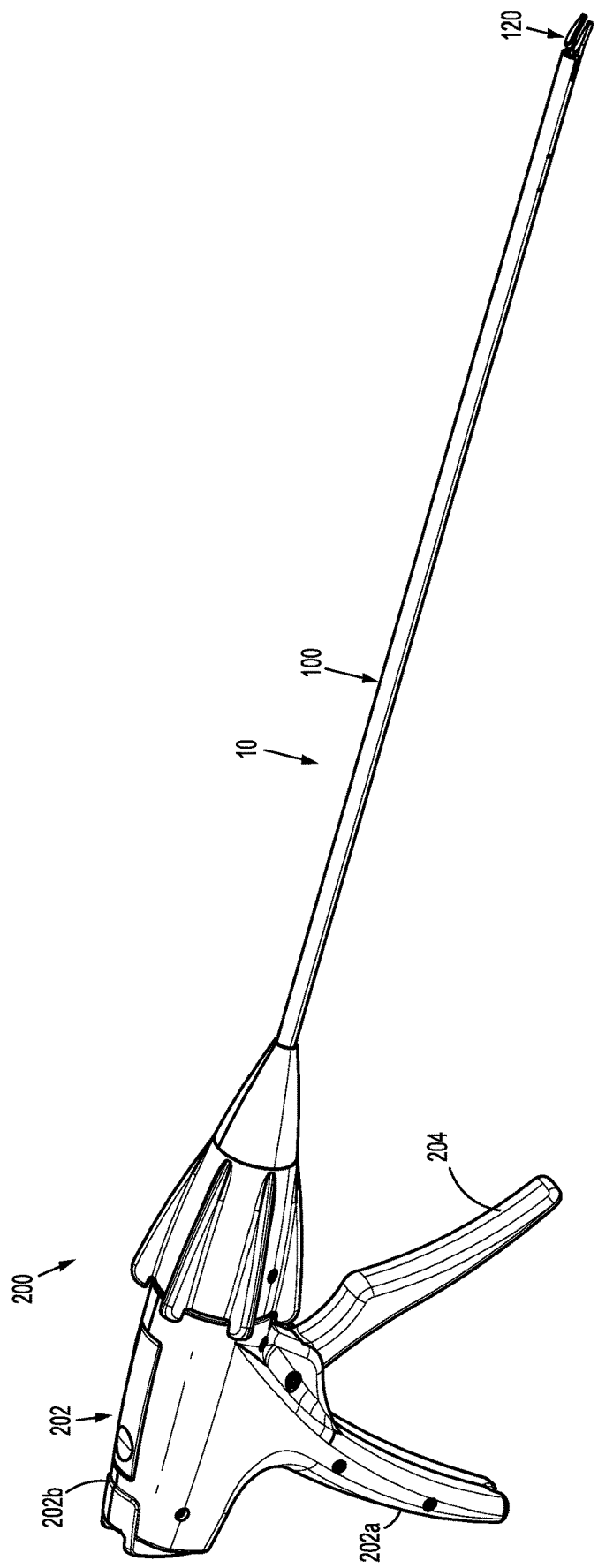
FIG. 1 is a perspective view of a reposable endoscopic surgical clip applier including a reusable handle assembly and a shaft assembly connected thereto.

Embodiments of endoscopic surgical clip appliers and shaft assemblies thereof, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
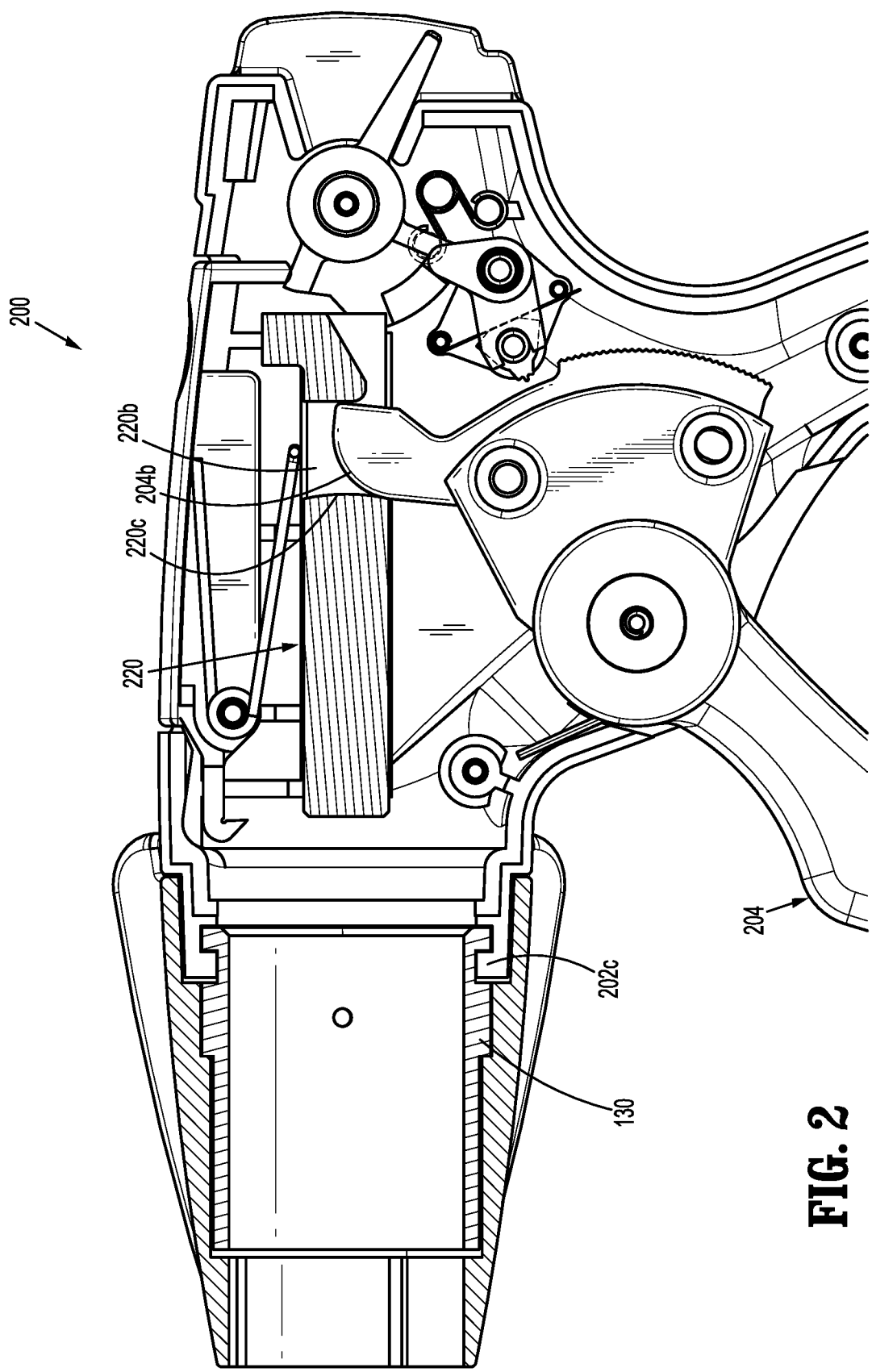
FIG. 2 is a perspective view of the handle assembly of FIG. 1 with at least a housing half-section removed therefrom.

With reference to FIGS. 1 and 2, an apparatus for application of surgical clips to body tissue is illustrated and designated 10. The apparatus or surgical clip applier 10 generally includes a reusable handle assembly 200 and a disposable shaft assembly 100 operably coupled to the handle assembly 200. The handle assembly 200 includes a housing 202 having a first or right side half-section 202a and a second or left side half-section 202b. Housing 202 of handle assembly 200 further includes or defines a nose 202c dimensioned for receipt of a hub 130 of shaft assembly 100. Housing 202 of handle assembly 200 may be formed of a suitable plastic or thermoplastic material. It is further contemplated that housing 202 of handle assembly 200 may be fabricated from stainless steel of the like.

Handle assembly 200 includes a trigger 204 pivotably supported between right side half-section 202a and left side half-section 202b of housing 202. Trigger 204 is biased by a biasing member (not explicitly shown) to bias or urge trigger 204 to the un-actuated condition. Trigger 204 includes a drive arm 204b extending therefrom. Drive arm 204b may be integrally formed therewith or may be separately and fixedly secured to trigger 204. Drive arm 204b may define a curved, radiused or filleted upper distal surface.

Handle assembly 200 further includes a drive plunger 220 operatively connected to trigger 204. Drive plunger 220 defines a proximally extending trigger slot 220b formed in a proximal portion thereof for operatively receiving drive arm 204b of trigger 204. Trigger slot 220b defines a distal surface or wall 220c against which a distal surface of drive arm 204b of trigger 204 contacts in order to distally advance drive plunger 220 during an actuation of trigger 204. Drive plunger 220 has a distal end operably coupled to a proximal end of a spindle 124 (FIG. 5) of shaft assembly 100 to effect axial movement of the spindle 124 upon actuation of the trigger 204 of handle assembly 200.

For a more detailed description of the components and operation of the handle assembly 200 of clip applier 10, reference may be made to, for example, U.S. Patent Application Publication No. 2017/0128071, the entire contents of which being incorporated by reference herein.

Figure 3:
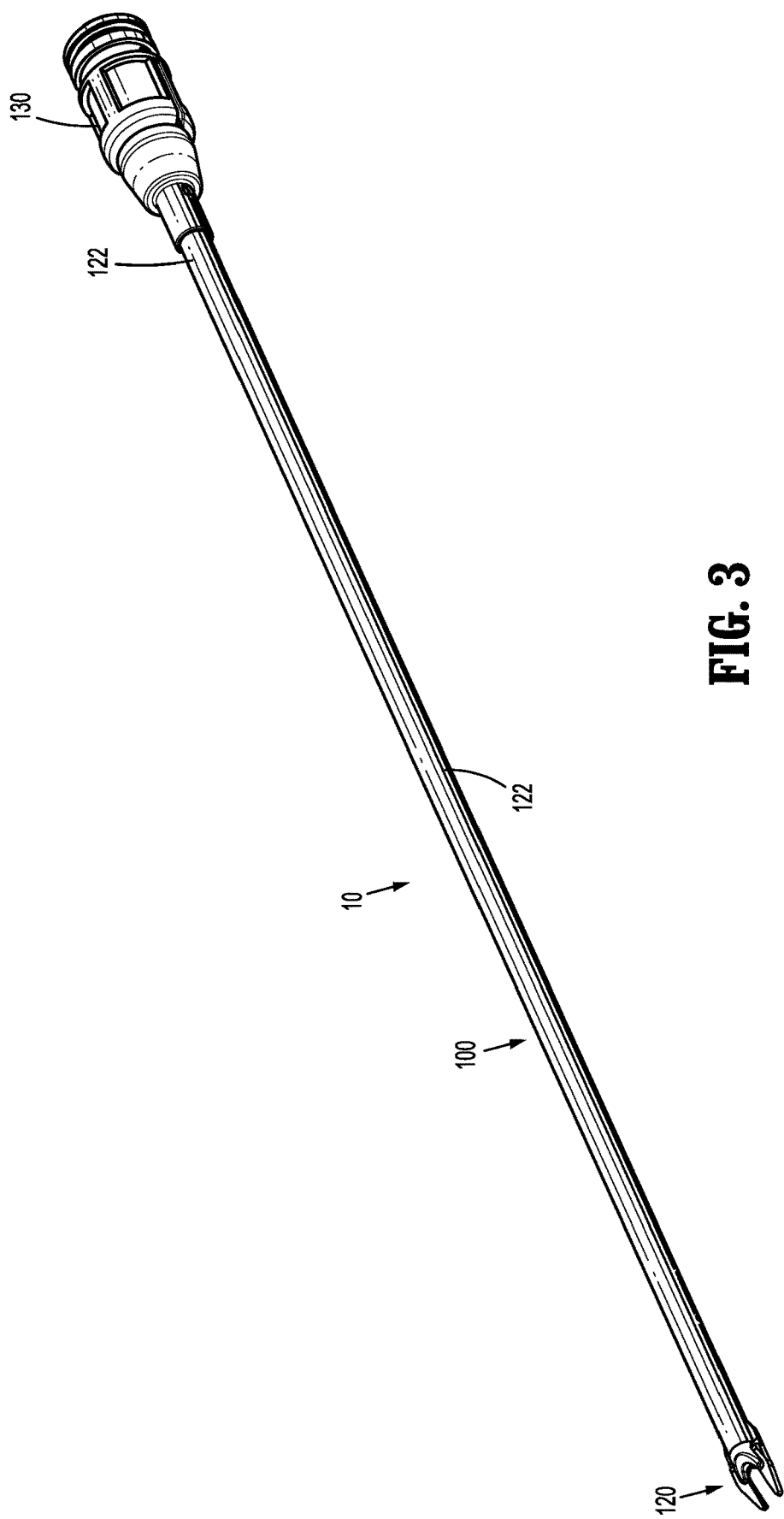
FIG. 3 is a perspective view of the shaft assembly of the endoscopic surgical clip applier of FIG. 1.
Figure 4:
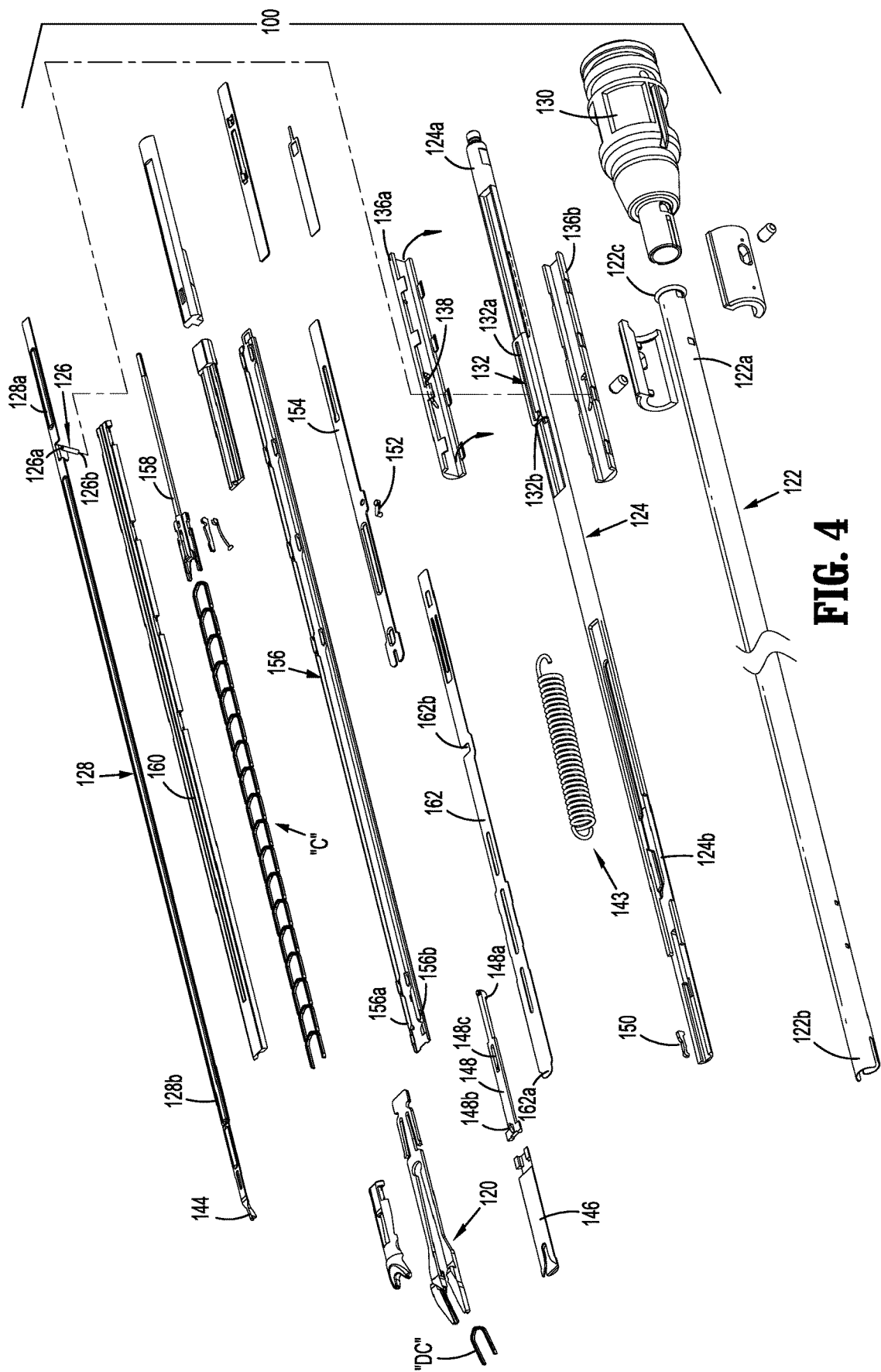
FIG. 4 is a perspective view, with parts separated, of the shaft assembly of FIG. 3.

With reference to FIGS. 3 and 4, the shaft assembly 100 of the clip applier 10 is operably coupled to the handle assembly 200 (FIGS. 1 and 2) for actuation by the handle assembly 200. The shaft assembly 100 stores a stack of surgical clips "C" therein and has a pair of jaws 120 configured to form, in seriatim, the surgical clips "C" received from a pusher bar 128 of the shaft assembly 100 upon actuation of the handle assembly 200. The shaft assembly 100 includes an elongated outer member or outer tube 122, an elongated spindle or inner shaft 124 axially movable within the outer tube 122 for actuating the clip applier 10, and a slidable member 126 movably coupled to the spindle 124 for axially translating the pusher bar 128 to load and hold the surgical clips "C" in the jaws 120 during clip formation, as will be described.

Figure 13:
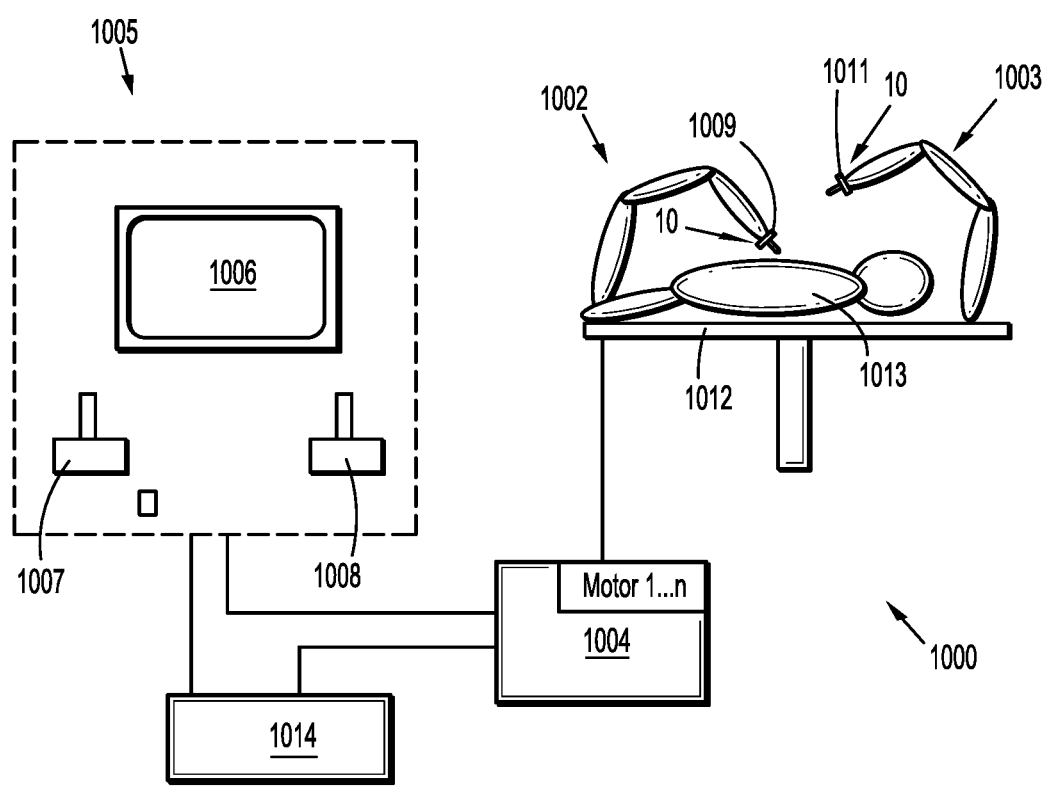
FIG. 13 is a schematic illustration of a robotic surgical system configured for use in accordance with the present disclosure.

The outer tube 122 of the shaft assembly 100 has a proximal portion 122a supported and secured to a hub 130, and a distal portion 122b supporting the jaws 120. The hub 130 may be configured to be coupled to the handle assembly 200 (FIGS. 1 and 2) or an actuator of a robotic system 1000 (FIG. 13). The outer tube 122 defines a lumen 122c extending longitudinally therethrough dimensioned for slidable receipt of the spindle 124.

With reference to FIGS. 4-11, the spindle or inner shaft 124 of the shaft assembly 100 is slidably supported within the lumen 122c of the outer tube 122 and has a generally elongated configuration. The spindle 124 includes a proximal portion 124a, and a distal portion 124b configured to selectively actuate the pair of jaws 120 during distal advancement of the spindle 124. The proximal portion 124a of the spindle 124 may define a hook, an enlarged head or other translational force coupling feature configured to be coupled to an actuator (e.g., the drive plunger 220 of the handle assembly 200 or an actuator of the robotic surgical system 1000).

The proximal portion 124a of the spindle 124 defines an elongate channel 132 extending longitudinally along the spindle 124. The channel 132 of the spindle 124 is dimensioned for slidable receipt of the slidable member 126, and has a first portion or proximal portion 132a and a second portion or distal portion 132b extending at a non-zero angle relative to the first portion 132a. The first portion 132a of the channel 132 has a linear configuration and extends parallel to a longitudinal axis "X" defined by the spindle 126. The second portion 132b of the channel 132 extends from the first portion 132a of the channel 132 perpendicularly relative to the longitudinal axis "X" of the spindle 126. In some embodiments, the second portion 132b of the channel 132 may extend at any suitable angle relative to the longitudinal axis "X." In embodiments, the second portion 132b of the channel 132 may be a notch extending laterally from the first portion 132a of the channel 132.

The proximal portion 124a of the spindle 124 has an inner surface 134 that defines the elongate channel 132. The inner surface 134 has a proximal wall 134a that defines a proximal limit of the second portion 132b of the channel 132, and a distal wall 134b that defines a distal limit of the second portion 132b of the channel 132. The second portion 132b of the channel 132 is dimensioned for receipt of the slidable member 126 during a first distal advancement of the spindle 124. The proximal wall 134a of the inner surface 134 is configured to push or urge the slidable member 126 distally therewith as the spindle 126 moves distally, and the distal wall 134b of the inner surface 134 is configured to push or urge the slidable member 126 proximally as the spindle 124 moves proximally, as will be described in greater detail.

With continued reference to FIGS. 4-11, the shaft assembly 100 further includes a pair of longitudinal half-sections or shafts 136a, 136b disposed on opposite sides of the proximal portion 124a of the spindle 124. The shafts 136a, 136b, when assembled, together may form a unitary tubular member that surrounds the proximal portion 124a of the spindle 124. The shafts 136a, 136b are fixed within the outer tube 122 of the shaft assembly 100, such that the shafts 136a, 136b remain axially fixed relative to the outer tube 122 during distal and proximal movement of the spindle 124 relative to the outer tube 122.

The first shaft 136a defines an elongate channel 138 extending longitudinally along the first shaft 136a and which is disposed adjacent the channel 132 of the spindle 124. The second shaft 136b also defines an elongate channel (not explicitly shown), similar to the channel 138 of the first shaft 136a. The channels 138 of the first and second shafts 136a, 136b are in mirrored relation to one another. The channel 138 of the first shaft 136a is dimensioned for slidable receipt of a first end portion 126a of the slidable member 126, whereas the channel of the second shaft 136b is dimensioned for slidable receipt of a second end portion 126b of the slidable member 126. Since the channels 138 of the first and second shafts 136a, 136b are in mirrored relation to one another, only the channel 138 of the first shaft 132 will be described in further detail herein.

The channel 138 of the first shaft 136a has a first portion or proximal portion 138a and a second portion or distal portion 138b extending at a non-zero angle relative to the first portion 138a. The first portion 138a of the channel 138 has a linear configuration and extends parallel to the longitudinal axis "X" defined by the spindle 124. The first portion 138a of the channel 138 of the first shaft 136a defines a plane that is offset (e.g., disposed above or below) a plane defined by the first portion 132a of the channel 132 of the spindle 124. The second portion 138b of the channel 138 bends or extends upwardly from the first portion 138a of the channel 138, and in some embodiments downwardly from the first portion 138a of the channel 138. In some embodiments, the second portion 138b of the channel 138 may bend or extend relative to the first portion 138a of the channel 138 and may have a linear configuration. In some embodiments, the second portion 138b of the channel 138 may have a curved configuration.

The second portion 138b of the channel 138 has a distal region 138c that is coplanar with the first portion 132a of the channel 132 of the spindle 124. In this way, when the slidable member 126 is disposed within the first portion 132a of the channel 132 of the spindle 124, the slidable member 126 is simultaneously disposed within the second portion 138b of the channel 138 of the shafts 136a, 136b. Similarly, when the slidable member 126 is disposed within the second portion 132b of the channel 132 of the spindle 124, the slidable member 126 is simultaneously disposed with the first portion 138a of the channel 138 of the shafts 136a, 136b.

Figure 6:
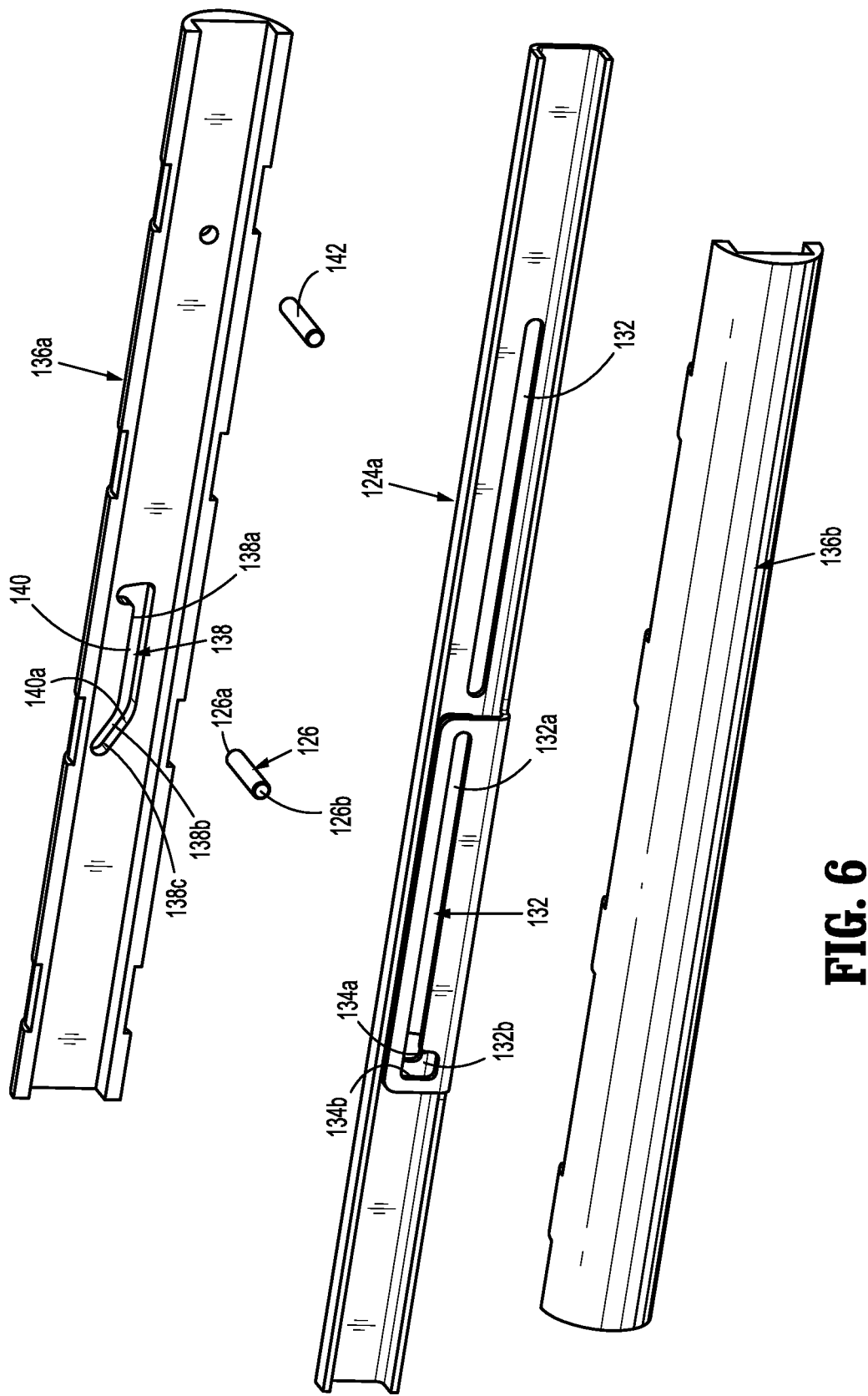
FIG. 6 is a perspective view, with parts separated, of the spindle, the slidable member, and left and right shafts of the shaft assembly of FIG. 5B.

With reference to FIG. 6, the first shaft 136a has an inner surface 140 that defines the elongate channel 138. The inner surface 140 has a ramped portion 140a that partially defines the second portion 138b of the channel 138 of the first shaft 136a. The ramped portion 140a extends upwardly from the first portion 138a of the channel 138 of the first shaft 136a and is configured to urge or cam the slidable member 126 upwardly into the distal region 138c of the second portion 138b of the channel 138 of the first shaft 136a as the slidable member 126 is moved distally by the proximal wall 134a of the spindle 124. As the ramped portion 140a cams the slidable member 126 upwardly into the distal region 138c of the channel 138 of the first shaft 136a, the slidable member 126 is also moved from the second portion 132b of the channel 132 of the spindle 124 into the first portion 132a of the channel 132 of the spindle 124.

The slidable member 126 of the shaft assembly 100 may be configured as a pin or bar having a first end portion 126a slidably disposed within the channel 138 of the first shaft 136a, an intermediate portion extending through the channel 132 of the spindle 124, and a second end portion 126b slidably disposed within the channel (not explicitly shown) of the second shaft 136b. As briefly mentioned above, when the slidable member 126 is simultaneously disposed within both the first portion 138a of the channel 138 of the shafts 136a, 136b and the second portion 132b of the channel 132 of the spindle 124, the slidable member 126 is axially movable relative to the shafts 136a, 136b in response to axial movement of the spindle 124 via the proximal and distal walls 134a, 134b of the spindle 124. In contrast, when the slidable member 126 is simultaneously disposed within both the second portion 138b of the channel 138 of the shafts 136a, 136b and the first portion 132a of the channel 132 of the spindle 124, the slidable member 126 is axially restrained within the second portion 138b of the channel 138 of the shafts 136a, 136b during axial movement of the spindle 124, whereby the slidable member 126 rides within the first portion 132a of the channel 132 of the spindle 124.

The shaft assembly 100 may include a fixed pin or rod 142 and a biasing member, such as, for example, an extension spring 143 (FIG. 4). The extension spring 143 has a proximal loop, and a distal loop having the sliding member 126 extending therethrough. The fixed pin 142 extends through a longitudinally-extending slot 133 defined by the proximal portion 124a of the spindle 124 and through the proximal loop of the extension spring 143. The slot 133 is disposed proximally of the channel 132 of the spindle 124. The fixed pin 142 has a first end portion fixed to the first shaft 136a, and a second end portion fixed to the second shaft 136b, such that the fixed pin 142 rides within the slot 133 of the spindle 124 during axial movement of the spindle 124. The proximal loop of the extension spring 143 is fixed to the fixed pin 142, and the distal loop of the extension spring 143 is fixed to the slidable member 126. As such, the extension spring 143 exerts a proximally-oriented force on the slidable member 126 to urge the slidable member 126, and in turn the pusher bar 128, toward a retracted position.

Figure 12:
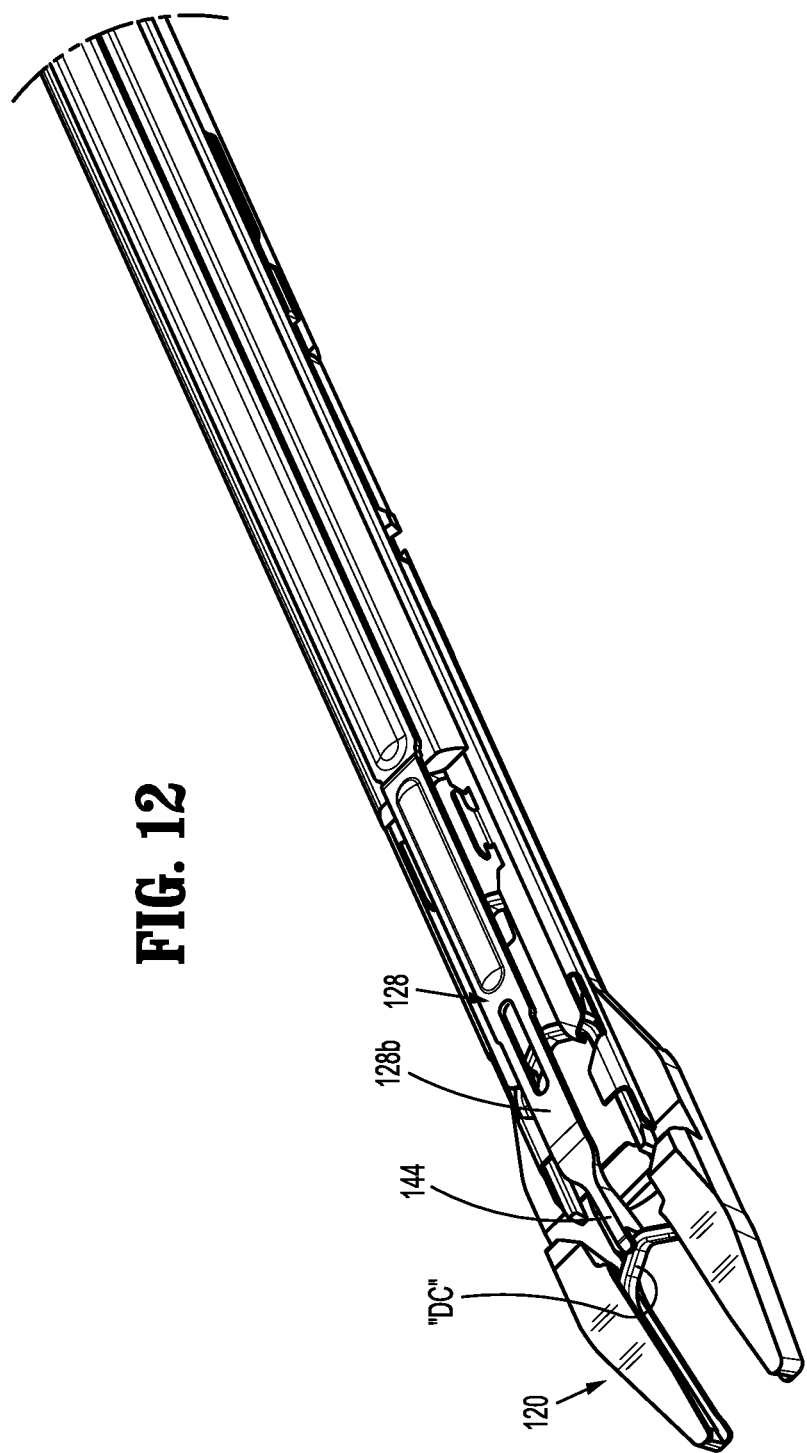
FIG. 12 is an enlarged view, with an outer tube removed, of a distal portion of the shaft assembly of FIG. 3.

With reference to FIGS. 4 and 12, the pusher bar 128 of the shaft assembly 100 has a proximal portion 128a, and a distal portion 128b for loading a distal-most surgical clip "DC" of the stack of surgical clips "C" between the jaws 120. The proximal portion 128a of the pusher bar 128 is fixed to the slidable member 126 so that the pusher bar 128 moves axially with axial movement of the slidable member 126. The proximal portion 128a of the pusher bar 128 may be fixed to the slidable member 126 via any suitable fastening engagement, such as, for example, various fasteners, adhesives, snap-fit engagements, or the like. Since the proximal portion 128a of the pusher bar 128 is fixed to the slidable member 126, axial movement of the slidable member 126 results in a corresponding axial movement of the pusher bar 128.

The distal portion 128b of the pusher bar 128 defines a pusher 144 configured to position the distal-most surgical clip "DC" between the pair of jaws 120 as the slidable member 126 is advanced toward a distal position, as shown in FIG. 9. The pusher 144 has a narrow profile for allowing the pair of jaws 120 to move to an approximated position while the pusher 144 is disposed therebetween. For example, the pusher 144 may have a width that is less than a horizontal distance the pair of jaws 120 are spaced from one another after completing a clip formation.

With continued reference to FIG. 4, additional components of the shaft assembly 100 responsible for effecting formation of the surgical clips "C" will be described. The distal portion 124b of the spindle 124 is operatively connected to a jaw cam closure wedge 146 via a slider joint 148. The jaw cam closure wedge 146 is selectively actuatable by the spindle 124 to engage camming features of the pair of jaws 120 to close the pair of jaws 120 and form a surgical clip "C" loaded therewithin. The slider joint 148 supports a latch member 150 for selective engagement with the spindle 124. The latch member 150 may be cammed in a direction toward the spindle 124 during actuation or translation of the spindle 124. In particular, during distal actuation of the spindle 124, at a predetermined distance, the latch member 150 is mechanically forced or cammed into and engaged with a slot in the spindle 124. This engagement of the latch member 150 in the slot of the spindle 124 allows the slider joint 148 to move together with the jaw cam closure wedge 146. The jaw cam closure wedge 146 thus can engage the relevant surfaces of the pair of jaws 120 to close the pair of jaws 120.

The slider joint 148 is connected, at a proximal portion 148a thereof, to a passageway formed in the distal portion 124b of the spindle 124. A distal portion 148b of the slider joint 148 defines a substantially T-shaped profile, wherein the distal portion 148b thereof is connected to the jaw cam closure wedge 146. The latch member 150 functions as a linkage and is disposed to move through an aperture 148c in the slider joint 148 to link with another fixed member and prevent the slider joint 148 from advancing the jaw cam closure wedge 146, and thus preventing the camming of the jaw cam closure wedge 146 from camming the pair of jaws 120 to a closed condition during an initial actuation of the clip applier 10. The distal portion 124b of the spindle 124 is provided with a camming feature configured to move a cam link 152 (pivotably connected to a filler component 154) in a perpendicular manner relative to a longitudinal axis of the spindle 124 during a distal advancement of the spindle 124.

The shaft assembly 100 further includes a clip channel 156 received within the outer tube 122. The clip channel 156 slidably retains the stack of surgical clips "C" therein for application, in seriatim, to the desired tissue or vessel. A clip follower 158 is provided and slidably disposed within the clip channel 156 at a location proximal of the stack of surgical clips "C." A spring (not shown) is provided to spring-bias the clip follower 158, and in turn, the stack of surgical clips "C", distally. A clip channel cover 160 is provided that overlies the clip channel 156 to retain and guide the clip follower 158, the spring, and the stack of surgical clips "C" in the clip channel 156.

The shaft assembly 100 further includes a wedge plate 162 that is biased to a proximal position by a wedge plate spring (not shown). The wedge plate 162 is a flat bar shaped member having a number of windows formed therein. The wedge plate 162 has a distal-most position wherein a tip or nose of the wedge plate 162 is inserted between the pair of jaws 120 to maintain the pair of jaws 120 in an open condition for loading of the distal-most surgical clip "DC" therein. The wedge plate 162 has a proximal-most position, maintained by the wedge plate spring, wherein the tip or nose of the wedge plate 162 is retracted from between the pair of jaws 120.

The wedge plate 162 defines a "U" or "C" shaped aperture or notch 162b in a side edge thereof. The C-shaped aperture or notch 162b of the wedge plate 162 selectively engages the cam link 152 supported on the filler plate 154. The cam link 152 selectively engages a surface of C-shaped aperture or notch 162b of the wedge plate 162 to retain the wedge plate 162 in a distal-most position such that a distal tip 162a of the wedge plate 162 is maintained inserted between the pair of jaws 120 to maintain the pair of jaws 120 splayed apart.

The filler component 154 of the shaft assembly 100 is interposed between the clip channel 156 and the wedge plate 162, at a location proximal of the pair of jaws 120. The filler component 154 pivotably supports the cam link 152 that is engagable with the wedge plate 162. During a distal advancement of the spindle 124, a camming feature of the spindle 124 engages a cam link boss of the cam link 152 to thereby move the cam link 152 out of engagement with the wedge plate 162 and permit the wedge plate 162 to return to the proximal-most position as a result of the spring.

It is contemplated that the clip applier 10 may be configured to close, fire, or form surgical clips similar to those shown and described in U.S. Patent Application Publication No. 2017/0128071, and U.S. Pat. No. 7,819,886 or 7,905,890, the entire contents of each of which are incorporated herein by reference.

In operation, the clip applier 10 is actuated to effect a stapling function thereof. In particular, the handle assembly 200 (FIGS. 1 and 2) or a control 1004 of a robotic assembly 1000 (FIG. 13) is actuated to advance the spindle 124 of the shaft assembly 100 in a distal direction within and relative to the outer tube 122. As shown in FIG. 7, when the clip applier 10 is in an initial, un-actuated state, the slidable member 126 of the shaft assembly 100 is disposed in the second portion or notch 132b of the channel 132 of the spindle 124 and the first portion 138a of the channel 138 of each of the first and second shafts 136a, 136b.

During a first distal movement of the spindle 124, in the direction indicated by arrow "A" in FIG. 7, the proximal wall 134a of the spindle 124 urges the slidable member 126 distally and through the first portion 138a of the channel 138 of each of the first and second shafts 136a, 136b. Since the pusher bar 128 is fixed to the slidable member 126, the pusher bar 128 also moves distally, whereby the pusher 144 (FIG. 12) of the distal portion 128b of the pusher bar 128 carries or pushes the distal-most surgical clip "DC" of the surgical clips "C" through the clip channel 156 in a distal direction until the distal-most surgical clip "DC" is disposed proximate the pair of jaws 120, signifying the conclusion of the first distal movement of the spindle 124, slidable member 126, and pusher bar 128.

After completion of the first distal movement of the spindle 124, the spindle 124 undergoes a second distal advancement or movement, via actuation of the handle assembly 200 or the control 1004 (FIG. 13), during which the slidable member 126 engages the ramped portion 140a of each of the first and second shafts 136a, 136b, as shown in FIG. 8. As the slidable member 126 engages the ramped portion 140a, the slidable member 126 is cammed or moved upwardly and into both the distal region 138c of the channel 138 of each of the first and second shafts 136a, 136b and the first portion 132a of the channel 132 of the spindle 124, as shown in FIG. 9.

Upon the slidable member 126 entering the distal region 138c of the channel 138 of the first and second shafts 136a, 136b, the pusher 144 (FIG. 12) of the pusher bar 128 positions the distal-most clip "DC" between the pair of jaws 120. With the slidable member 126 captured within both the distal region 138c of the channel 138 of the first and second shafts 136a, 136b and the first portion 132a of the channel 132 of the spindle 124, a third distal movement of the spindle 124 does not result in axial movement of the slidable member 126. As such, while the spindle 124 moves distally acting on the jaw cam closure wedge 146 to approximate the jaws 120 to form the distal-most surgical clip "DC," the pusher 144 of the pusher bar 128 remains engaged with the distal-most surgical clip "DC" due to the slidable member 126 being axially restrained within both the distal region 138c of the channel 138 of the first and second shafts 136a, 136b and the first portion 132a of the channel 132 of the spindle 124.

To reset the clip applier 10, the spindle 124 is retracted proximally, in the direction indicated by arrow "B" in FIG. 10, within the outer tube 122 and out of engagement with the jaws 120 to allow the jaws 120 to expand (due to their own spring bias) to their open configuration. Proximal movement of the spindle 124 relative to the slidable member 126 and the pusher bar 128 is continued until the distal wall 134b of the proximal portion 124a of the spindle 124 contacts the slidable member 126, as shown in FIG. 10. As such, a continued proximal retraction of the spindle 124 results in the slidable member 126 and the attached pusher bar 128 moving downwardly and proximally along the ramped portion 140a of the first and second shafts 136a, 136b, and positioning the slidable member 126 in both the second portion 132b of the channel 132 of the spindle 124 and the first portion 138a of the channel 138 of each of the shafts 136a, 136b. Upon moving the slidable member 126 proximally, the pusher 144 of the pusher bar 128 is removed from between the jaws 120, resetting the clip applier 10. In addition, the biasing member that interconnects the slidable member 126 and the fixed pin 142 assists in retracting the slidable member 126.

It is contemplated, and within the scope of the present disclosure, that other endoscopic assemblies, including a pair of jaws having a unique and diverse closure stroke length thereof, may be provided with a drive assembly, similar to any of the drive assemblies described herein, for accommodating and adapting the closure stroke length for the pair of jaws thereof to the constant trigger stroke length.

Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

Surgical instruments such as the clip appliers described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Referring to FIG. 12, a medical work station is shown generally as robotic system or work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, the shaft assembly 100 of FIGS. 1-11, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the shaft assembly 100, execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of the shaft assembly 100. Medical work station 1000 may also include more than two robot arms 1002, 1003, the additional robot arms likewise being connected to control device 1004 and being telemanipulatable by means of operating console 1005. A surgical end effector, such as, for example, the shaft assembly 100 (FIGS. 1-11), may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023, the entire content of which is incorporated herein by reference, for a more detailed description of the construction and operation of an exemplary robotic surgical system.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
    a handle assembly; and
    a shaft assembly selectively connectable to the handle assembly and actuatable upon actuation of the handle assembly, the shaft assembly including:
        a pair of jaws movable between a spaced-apart position and an approximated position;
        an elongated spindle having a proximal portion configured to be coupled to an actuator of the handle assembly, and a distal portion operably coupled to the pair of jaws to selectively approximate the pair of jaws during distal movement of the spindle, the spindle defining a longitudinally-extending channel having a first portion, and a second portion extending at a non-zero angle relative to the first portion;
        a first shaft disposed alongside the spindle and defining a longitudinally-extending channel having a first portion, and a second portion extending at a non-zero angle relative to the first portion of the channel of the first shaft;
        a slidable member extending through each of the channels of the spindle and the first shaft, wherein a first distal movement of the spindle relative to the first shaft moves the slidable member with the spindle and through the first portion of the channel of the first shaft, and a second distal movement of the spindle relative to the first shaft moves the slidable member with the spindle and into the second portion of the channel of the first shaft and the first portion of the channel of the spindle, such that a third distal movement of the spindle relative to the first shaft moves the spindle distally relative to the slidable member; and a pusher bar having a proximal portion fixedly coupled to the slidable member, and a distal portion configured to load a distal-most surgical clip into the pair of jaws during distal movement of the slidable member, via the first distal movement of the spindle, and remain in a distally advanced position during approximation of the pair of jaws.

2. The apparatus according to claim 1, wherein the first portion of the channel of each of the spindle and the first shaft has a linear configuration and extends parallel to a longitudinal axis defined by the spindle, and the second portion of the channel of each of the spindle and the first shaft extends at a non-parallel angle relative to the longitudinal axis of the spindle.

3. The apparatus according to claim 1, wherein the shaft assembly further includes a second shaft disposed on an opposite side of the proximal portion of the spindle as the first shaft and being fixedly coupled to the first shaft, the second shaft defining a longitudinally-extending channel in mirrored relation with the channel of the first shaft, wherein the slidable member has a first end portion movably disposed within the channel of the first shaft, and a second end portion movably disposed within the channel of the second shaft.

4. The apparatus according to claim 1, wherein the first portion of the channel of the spindle defines a first plane, and the first portion of the channel of the first shaft defines a second plane offset from the first plane of the first portion of the channel of the spindle.

5. The apparatus according to claim 4, wherein at least a distal region of the second portion of the channel of the first shaft is coplanar with the first plane of the first portion of the channel of the spindle.

6. The apparatus according to claim 1, wherein the second portion of the channel of the spindle has a proximal limit defined by a proximal wall, the proximal wall configured to contact the slidable member during the first distal movement of the spindle to distally move the slidable member relative to the first shaft.

7. The apparatus according to claim 6, wherein the second portion of the channel of the spindle has a distal limit defined by a distal wall, the distal wall configured to contact the slidable member during proximal movement of the spindle relative to the first shaft.

8. The apparatus according to claim 1, wherein the first shaft includes a ramped inner surface that defines the second portion of the channel of the first shaft, the ramped inner surface being configured to move the slidable member upwardly from the second portion of the channel of the spindle into the first portion of the channel of the spindle during the second distal movement of the spindle.

9. The apparatus according to claim 1, wherein the slidable member is axially restrained within the second portion of the channel of the first shaft during the third distal movement of the spindle, such that the pusher bar is axially fixed relative to the pair of jaws during the third distal movement of the spindle.

10. The apparatus according to claim 9, wherein the slidable member rides within the first portion of the channel of the spindle during the third distal movement of the spindle.

11. A shaft assembly of an apparatus for applying surgical clips to body tissue, the shaft assembly comprising:

a pair of jaws movable between a spaced-apart position and an approximated position;

an elongated spindle having a proximal portion configured to be coupled to an actuator of the handle assembly, and a distal portion operably coupled to the pair of jaws to selectively approximate the pair of jaws during distal advancement of the spindle, the spindle defining a longitudinally-extending channel having a first portion, and a second portion extending at a non-zero angle relative to the first portion;

a first shaft disposed alongside the spindle and defining a longitudinally-extending channel having a first portion, and a second portion extending at a non-zero angle relative to the first portion of the channel of the first shaft;

a slidable member extending through each of the channels of the spindle and the first shaft, wherein a first distal movement of the spindle relative to the first shaft moves the slidable member with the spindle and through the first portion of the channel of the first shaft, and a second distal movement of the spindle relative to the first shaft moves the slidable member with the spindle and into the second portion of the channel of the first shaft and the first portion of the channel of the spindle, such that a third distal movement of the spindle relative to the first shaft moves the spindle distally relative to the slidable member; and a pusher bar having a proximal portion fixedly coupled to the slidable member, and a distal portion configured to load a distal-most surgical clip into the pair of jaws during distal movement of the slidable member, via the first distal movement of the spindle, and remain in a distally advanced position during approximation of the pair of jaws.

12. The shaft assembly according to claim 11, wherein the first portion of the channel of each of the spindle and the first shaft has a linear configuration and extends parallel to a longitudinal axis defined by the spindle, and the second portion of the channel of each of the spindle and the first shaft extends at a non-parallel angle relative to the longitudinal axis of the spindle.

13. The shaft assembly according to claim 11, further comprising a second shaft disposed on an opposite side of the proximal portion of the spindle as the first shaft and being fixedly coupled to the first shaft, the second shaft defining a longitudinally-extending channel in mirrored relation with the channel of the first shaft, wherein the slidable member has a first end portion movably disposed within the channel of the first shaft, and a second end portion movably disposed within the channel of the second shaft.

14. The shaft assembly according to claim 11, wherein the first portion of the channel of the spindle defines a first plane, and the first portion of the channel of the first shaft defines a second plane offset from the first plane of the first portion of the channel of the spindle.

15. The shaft assembly according to claim 14, wherein at least a distal region of the second portion of the channel of the first shaft is coplanar with the first plane of the first portion of the channel of the spindle.

16. The shaft assembly according to claim 11, wherein the second portion of the channel of the spindle has a proximal limit defined by a proximal wall, the proximal wall configured to contact the slidable member during the first distal movement of the spindle to distally move the slidable member relative to the first shaft.

17. The shaft assembly according to claim 16, wherein the second portion of the channel of the spindle has a distal limit defined by a distal wall, the distal wall configured to contact the slidable member during proximal movement of the spindle relative to the first shaft.

18. The shaft assembly according to claim 11, wherein the first shaft includes a ramped inner surface that defines the second portion of the channel of the first shaft, the ramped inner surface being configured to move the slidable member upwardly from the second portion of the channel of the spindle into the first portion of the channel of the spindle during the second distal movement of the spindle.

19. The shaft assembly according to claim 11, wherein the slidable member is axially restrained within the second portion of the channel of the first shaft during the third distal movement of the spindle, such that the pusher bar is axially fixed relative to the pair of jaws during the third distal movement of the spindle.

20. The shaft assembly according to claim 19, wherein the slidable member rides within the first portion of the channel of the spindle during the third distal movement of the spindle.

* * * * *